(12) United States Patent
Kelly

(10) Patent No.: US 12,121,470 B1
(45) Date of Patent: Oct. 22, 2024

(54) DISPOSABLE TUBE FOR USE DURING OSTOMY APPLIANCE ATTACHMENT

(71) Applicant: Mark A Kelly, Frontenac, MO (US)

(72) Inventor: Mark A Kelly, Frontenac, MO (US)

( * ) Notice: Subject to any disclaimer, the term of this patent is extended or adjusted under 35 U.S.C. 154(b) by 0 days.

(21) Appl. No.: 18/735,686

(22) Filed: Jun. 6, 2024

Related U.S. Application Data

(63) Continuation-in-part of application No. 17/837,672, filed on Jun. 10, 2022, now abandoned.

(60) Provisional application No. 63/209,083, filed on Jun. 10, 2021.

(51) Int. Cl.
*A61F 5/445* (2006.01)
*A61F 5/44* (2006.01)

(52) U.S. Cl.
CPC ...... *A61F 5/445* (2013.01); *A61F 2005/4402* (2013.01)

(58) Field of Classification Search
CPC ........ A61F 5/445; A61F 5/441; A61F 5/4405; A61F 5/4407; A61F 2005/4402; A61M 1/60; A61M 1/63; A61M 1/64; A61M 1/68; A61M 1/682; A61M 1/684
See application file for complete search history.

(56) References Cited

U.S. PATENT DOCUMENTS

| | | | |
|---|---|---|---|
| 3,520,301 A | 7/1970 | Fenton | |
| 4,187,850 A | 2/1980 | Gust | |
| 4,344,433 A | 8/1982 | Smith | |
| 6,409,709 B1 | 6/2002 | Recto | |
| 8,343,119 B2 * | 1/2013 | Mayer | A61F 5/443 604/338 |
| 10,357,394 B2 | 7/2019 | Guidry et al. | |
| 10,478,328 B2 | 11/2019 | Guidry et al. | |
| 2010/0145292 A1 | 6/2010 | Meyer | |
| 2012/0277700 A1 | 11/2012 | Amer, Jr. et al. | |
| 2021/0244497 A1 | 8/2021 | Taweh | |

FOREIGN PATENT DOCUMENTS

| CN | 209059622 U | 7/2019 |
|---|---|---|
| GB | 2595893 B | 7/2022 |

OTHER PUBLICATIONS

Translation of CN 209059622.
European Patent Report Aug. 8, 2023.

* cited by examiner

*Primary Examiner* — Leslie A Lopez
*Assistant Examiner* — Timothy L Flynn
(74) *Attorney, Agent, or Firm* — Grace J. Fishel

(57) ABSTRACT

A disposable cupping tube for collecting fluid from a stoma with a hollow compressible cone seated on a rigid hollow stepped conical frustrum having an upper tier and lower tier. The lower tier having an inner wall sloped at a lower angle than the outside wall to maximize the contact area with the periphery of a stoma when the cone is compressed and the base of the stepped conical frustrum is passed over the stoma and pressed against the peristomal skin. An effective air seal is formed between the contact area and the stoma and between the base of the lower tier with the peristomal skin which is pulled up and around the base by the vacuum. A disc with perforations inserted into the lower tier divides the cupping tube into an upper and lower chamber when present.

10 Claims, 7 Drawing Sheets

DISPOSABLE TUBE FOR USE DURING OSTOMY APPLIANCE ATTACHMENT

BACKGROUND OF THE INVENTION

Field of the Invention

The present invention relates to a cupping tube for collection of waste from a stoma during installation and replacement of a two-piece ostomy appliance.

Brief Description of the Prior Art

Modern two-piece ostomy appliances include a mounting plate, commonly called a ring wafer or base plate, and a collection pouch that is attached mechanically to the ring wafer or with an adhesive. Urine from a stoma drains into the collection pouch which may be emptied or changed a number of times whereas the ring wafer may last between 4 to 10 days before it needs to be replaced.

A problem for urostomy patients with the current systems is that during removal and replacement of the mounting plate, urine flows from the stoma and wets the patient's skin around the stoma. The urine can irritate the patient's skin, possibly start an infection in the stoma, and will interfere with the adhesive bonding of a replacement ring wafer. Replacing a ring wafer and making the area clean and dry is difficult especially for elderly people who are most likely to be a urostomy patient. There is also an insurance problem. If a ring wafer fails because it is not applied to dry skin, Medicare and other insurance carriers limit the number of ostomy appliances covered per period and ostomy appliances are expensive if they must be privately paid for. Similar problems are encountered by ileostomy and colostomy patients.

BRIEF SUMMARY OF THE INVENTION

In view of the above, it is an object of the present invention to provide a collection tube that facilitates installation and replacement a two-piece ostomy appliance by a patient or his or her care providers. Other objects and features of the invention will be in part apparent and in part pointed out hereinafter.

In accordance with the invention a cupping tube includes a hollow cone seated on a hollow stepped conical frustrum. The cone is formed of a flexible or compressible material and the stepped conical frustrum is formed of a rigid or non-compressible material. In an embodiment, the cone and stepped conical frustrum are formed of a plastic material. The stepped conical frustrum has an upper and a lower tier with the lower tier having an outer wall with a flat upper surface upon which a base of the cone is seated. In most applications, the lower tier has an inner wall that slopes outwardly towards a base of the stepped conical frustrum at a lower angle than an outer wall makes to the lower base of the stepped conical frustrum to maximize contact area with a base of the stoma.

In some applications a disc in inserted into an upper base of the lower tier with at least one perforation dividing the cupping tube into a upper and lower chamber. In another aspect the disc has a retaining ring around an outer edge snap fitted into a groove in an inner surface of the lower tier.

The invention summarized above comprises the constructions hereinafter described, the scope of the invention being indicated by the subjoined claims.

BRIEF DESCRIPTION OF THE SEVERAL VIEWS OF THE DRAWINGS

In the accompanying drawings, in which one of various possible embodiments of the invention is illustrated, corresponding reference characters refer to corresponding parts throughout the several views of the drawings in which.

DETAILED DESCRIPTION OF AT LEAST ONE PREFERRED EMBODIMENT OF THE INVENTION

Figures 1, 2:
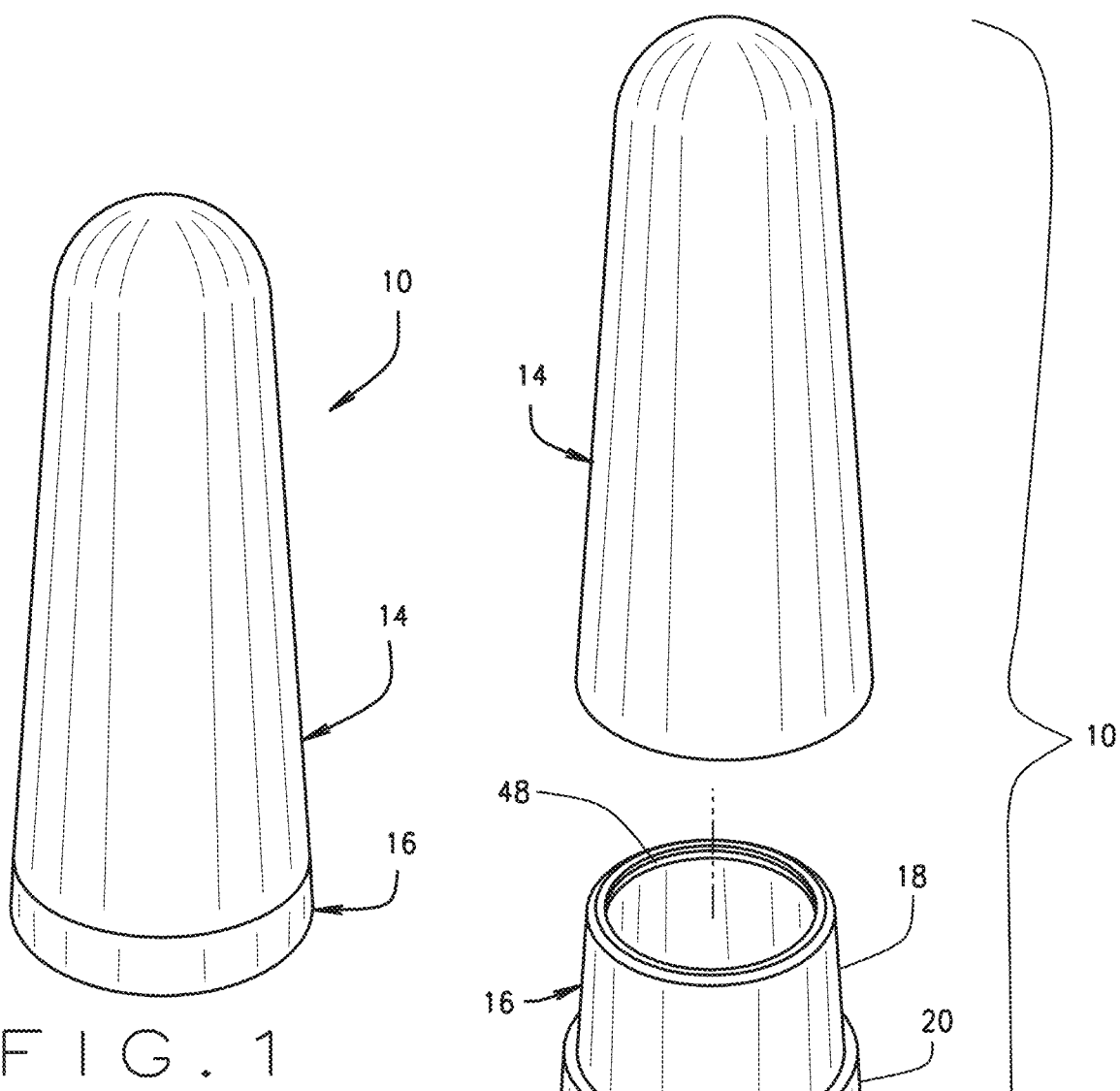
FIG. 1 is a perspective view of a cupping tube in accordance with the present invention.
FIG. 2 is an exploded view thereof.

Referring to the drawings more particularly by reference character, a cupping tube 10 for use during replacement of a ring wafer 12 in a two-piece ostomy application includes a hollow cone 14 formed of a flexible or compressible material and a hollow stepped conical frustrum 16 formed of a rigid or non-compressible material. The material for cone 14 and stepped conical frustrum 16 may be plastic.

Figure 5:
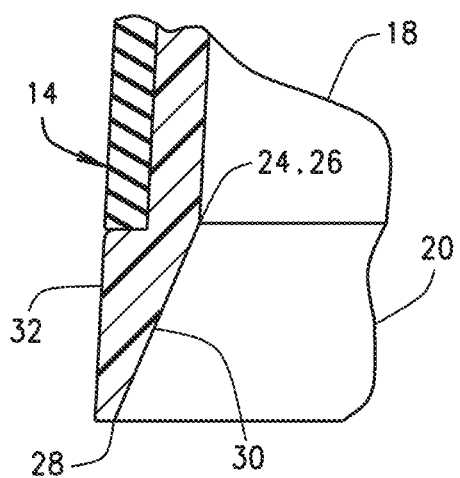
FIG. 5 is a detail taken along the line 5-5 in FIG. 3

As shown in the drawings, stepped conical frustrum 16 may be viewed has two cone frustrums stacked on top of each other. This structure results in an upper tier 18 and a lower tier 20 rather than a smooth, continuous taper. Upper tier 18 has an upper base 22 and a lower base 24 which may be circular and parallel to each other. In like manner lower tier 20 has an upper base 26 and a lower base 28. As best seen in FIG. 5, an inner wall 30 of lower tier 20 makes a lower angle (seen at 87°) at lower base 28 than outer wall 32 lower tier 28 maximize contact a contact area 34 with a stoma 36 as more particularly described below. In general angles between 6° and 90° may be suitable.

A disc 38 may be inserted into upper base 26 of lower tier 20 serving as a diaphragm to divide cupping tube 10 into an upper 40 and lower 42 chamber. As shown seen in FIG. 2, disc 38 has at least one perforation 44 but a plurality may be preferred as a guard against the possibility that fluid flow might be blocked by clotted material. On the other hand, perforations 44 are preferably small such that reverse flow through the perforations is blocked as discussed below.

Figure 3:
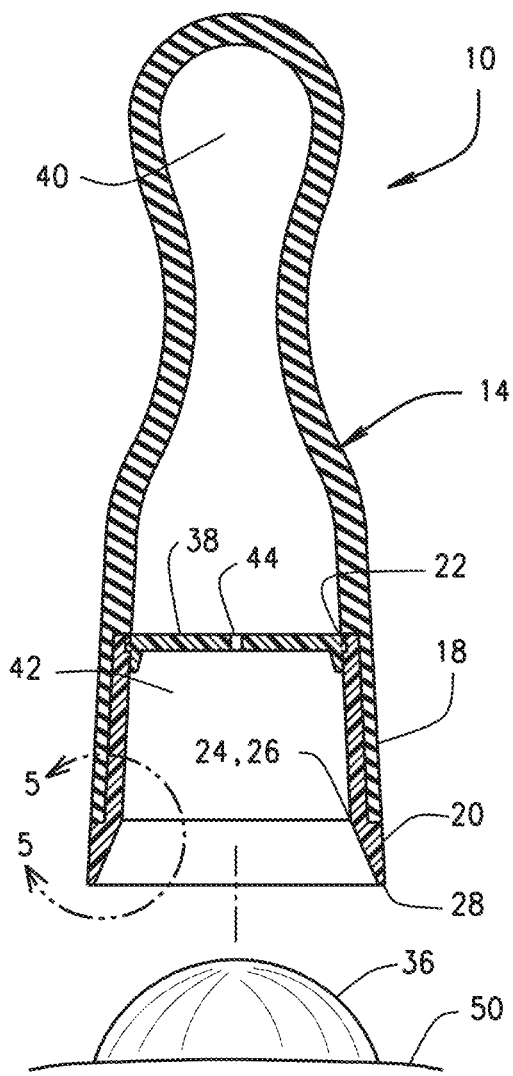
FIG. 3 is a cross section of the cupping tube positioned to be installed on a stoma.
Figure 4:
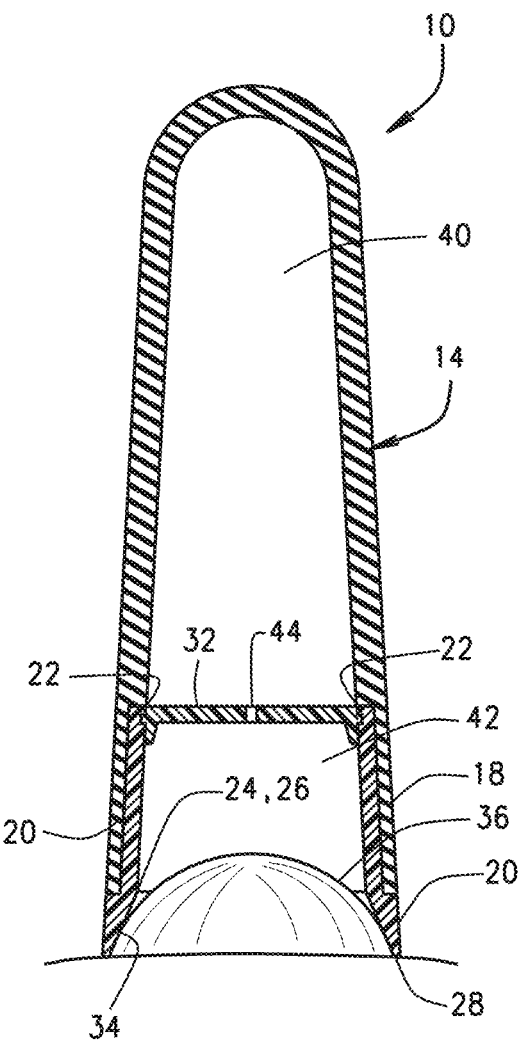
FIG. 4 a cross section of the cupping tube installed over a stoma.

With continuing reference to FIG. 2, disc 38 has a retaining ring 46 around an outer edge for snap fit in upper base 26 of lower tier 20. Turning to FIG. 3-4, a groove 48 is provided in an inner surface of lower tier 20 for snap fit of retaining ring 46 to provide an easily made and secure joint.

As shown in FIGS. 3 and 4, stoma 36 is generally dome shaped and has a texture somewhat the inside of a person's mouth. In use, cone 14 is pinched closed and lower base 28 of lower tier 20 passed over stoma 36 and pressed against the peristomal skin 50. As pressure on cone 14 is released a vacuum is drawn and inner wall 30 of lower tier 20 presses against rounded sides of stoma 36 and peristomal skin 50 drawn up and around lower base 28 forming a substantially air tight seal while the balance of the stoma is untouched. With a cylinder, a cupping tube only makes point contact at the base of the stoma whereas angled inner wall 30 provides a broad contact area 34 that results in a uniform pressure distribution and a good air seal. Patients requiring an ostomy tend to be older with folded, loose skin which in many cases is underlain with fat. In these patients peristomal skin 50 is partially sucked around and partially into lower base 28 completing the air seal.

In the embodiment shown in the drawings, cone 14 is formed of Santopreme 8211-35, has a height of 2.75 inches and a wall thickness of 0.125 inch. Stepped conical frustrum 16 is formed acrylonitrile butadiene styrene, has a height of 1.00 inch, an inside diameter of 0.966 inch at lower base of lower tier and an outside diameter of 1.142 inch. It will be understood that the above dimensions are illustrative and not binding as cupping tubes may be formed to accommodate different sized stomas, for example from less than 1 inch to more than 2 inches in inside diameter of lower base 28 in the case of urostomy.

As shown in FIGS. 6-15 and more particularly discussed below, urine collects in cupping tube 10 from stoma 36 during installation and replacement of a two-piece ostomy appliance. When disc 38 is present cupping and since the upper chamber is larger than the lower chamber, the bulk of the urine is in the upper chamber. When cupping tube 10 is detached from the skin, a small amount of urine in the lower chamber leaks onto the patient's skin which can be easily wiped up. The reduced size of perforations 44 in disc 38, keeps the majority of the urine in upper chamber 40 until the tube can be turned down side up and disposed of. The small mount of urine from the lower chamber does not interfere with placement of the attachment flange which will have occurred earlier on dry skin.\

Figure 6:
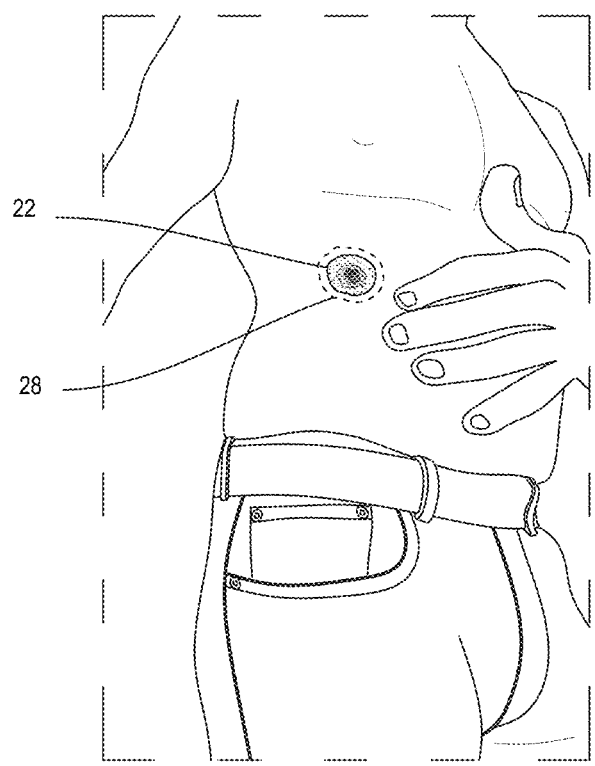
FIG. 6 is a view of a patient with a stoma in his sidewall.
Figure 7:
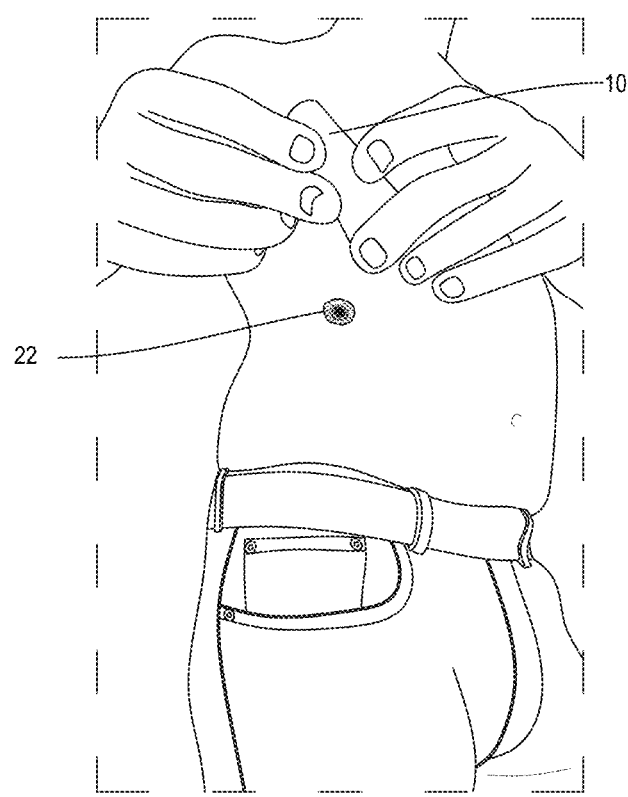
FIG. 7 is a view of the patient squeezing a cupping tube for attachment to his sidewall over the stoma.
Figure 8:
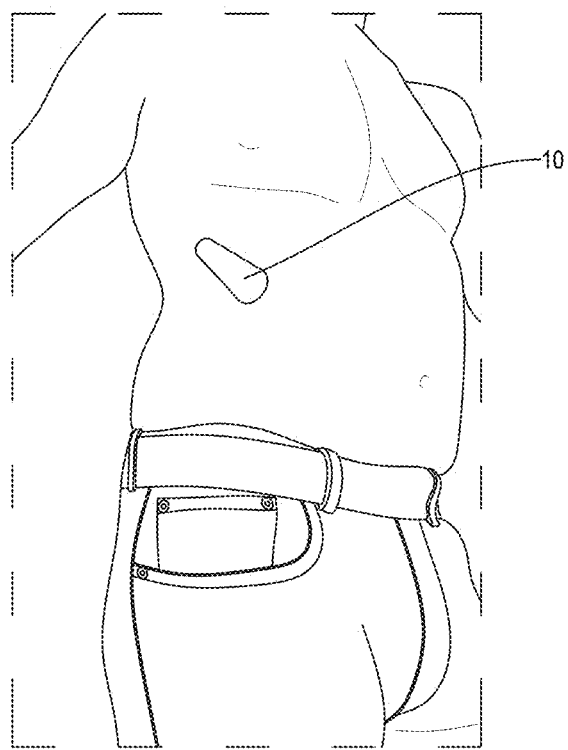
FIG. 8 shows the cupping tube installed over the stoma.

With continuing reference to FIGS. 6-15, the first steps in the procedure are to remove the used pouch and then detach the adhesively attached ring wafer to which the pouch was attached. Stoma 20 of a urostomy patient has no sphincter such that urine will continuous ooze from the stoma. With the present system, cupping tube 10 is positioned over the stoma as soon as the pouch is removed and the existing ring wafer detached from the skin and slid over cupping tube 10. Alternatively, the spent ring wafer may be removed first and then cupping tube 10 attached as shown in FIGS. 6-8.

During attachment, cupping tube 10 is squeezed (FIG. 7) and the open end (lower base 24 of lower tier 20) pressed against peristomal skin 50 (FIG. 8) to form an airtight seal. During initial healing, a user may have catheters extending from the stoma. In which case disc 38 is not inserted into cupping tube 10 or if present removed, lower base 28 of lower tier 20 of is passed over the stoma and catheters which are received in larger upper chamber 40. With cupping tube 10 attached, urine seeping from stoma 20 is drawn into upper chamber 40 through perforations 44 in disc 38.

Once the spent ring wafer is removed and cupping tube 10 attached, a user or his or her caretaker may take as much time as necessary to clean and prep the skin around the stoma. Without cupping tube 10, a pad is usually applied to the stoma in an attempt to soak up the urine. Application of a pad may mechanically injure the stoma and some urine is likely to escape the pad. This makes it very difficult to effectively clean the skin and prepare a dry skin surface necessary for attachment of replacement ring wafer 12. With cupping tube 10, prepping the skin is much easier.

Figure 9:
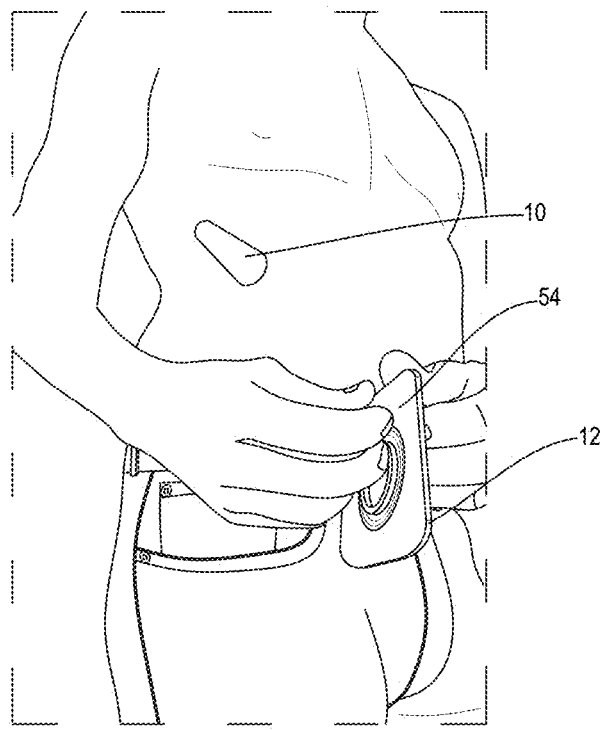
FIG. 9 is a view of the patient peeling a backing tape from a ring wafer to reveal an adhesive layer.
Figure 10:
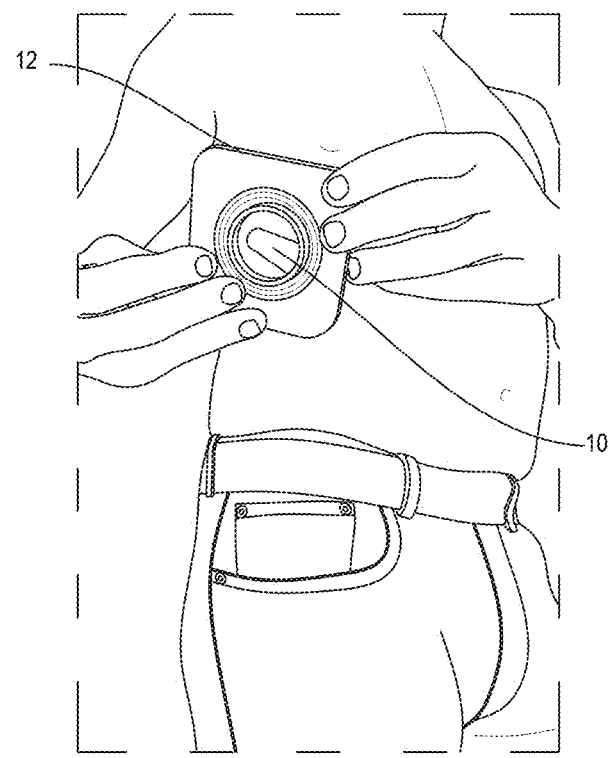
FIG. 10 shows the patient sliding the ring wafer over the cupping tube.
Figure 11:
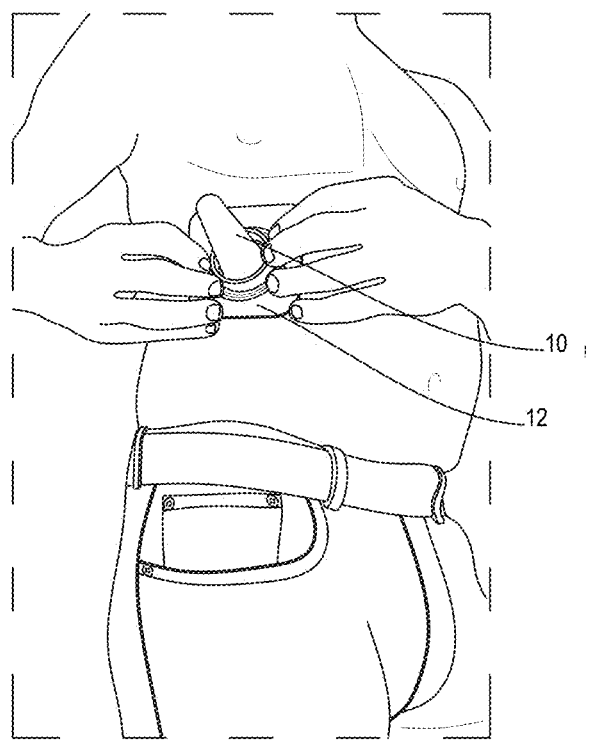
FIG. 11 is a view of the patient making sure that the ring wafer has proper orientation.
Figure 12:
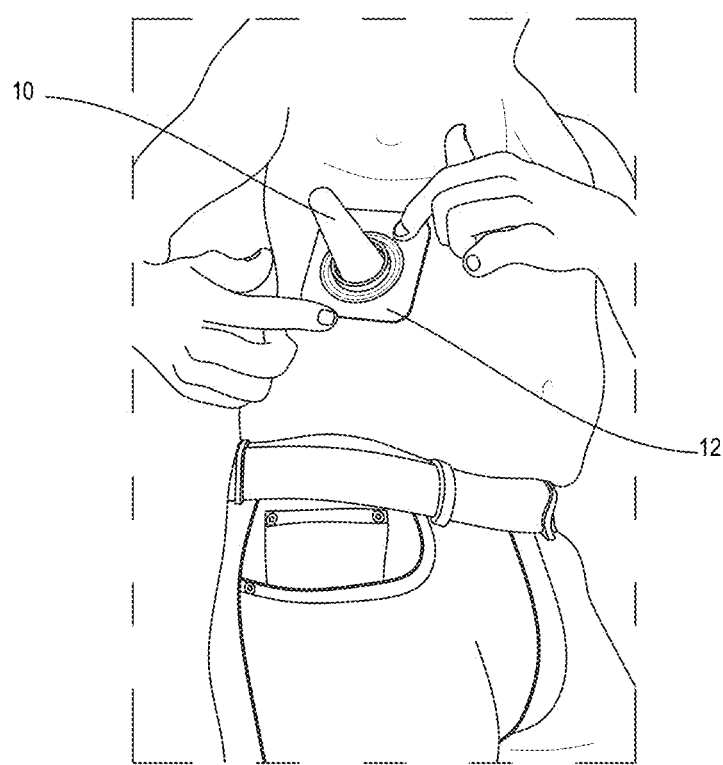
FIG. 12 shows the patient pressing the ring wafer down to adhesively secure the wafer to his chest.
Figure 13:
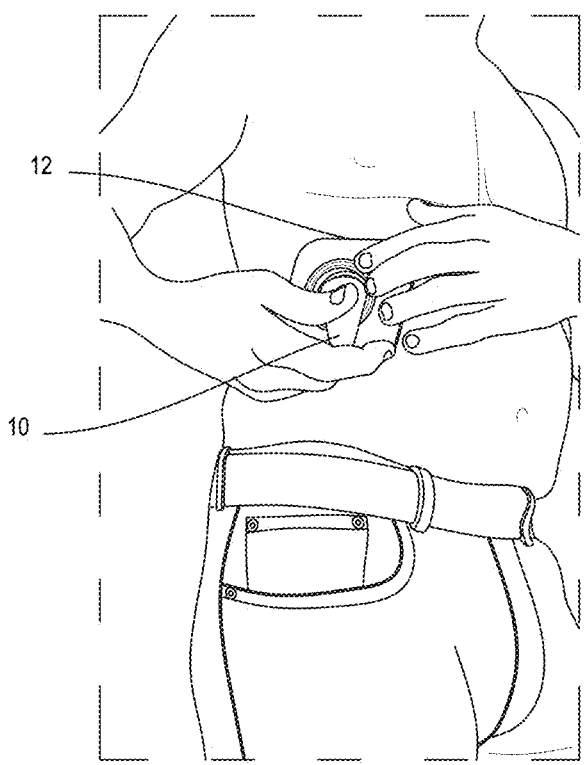
FIG. 13 shows the patient detaching the cupping tube from his chest.
Figure 14:
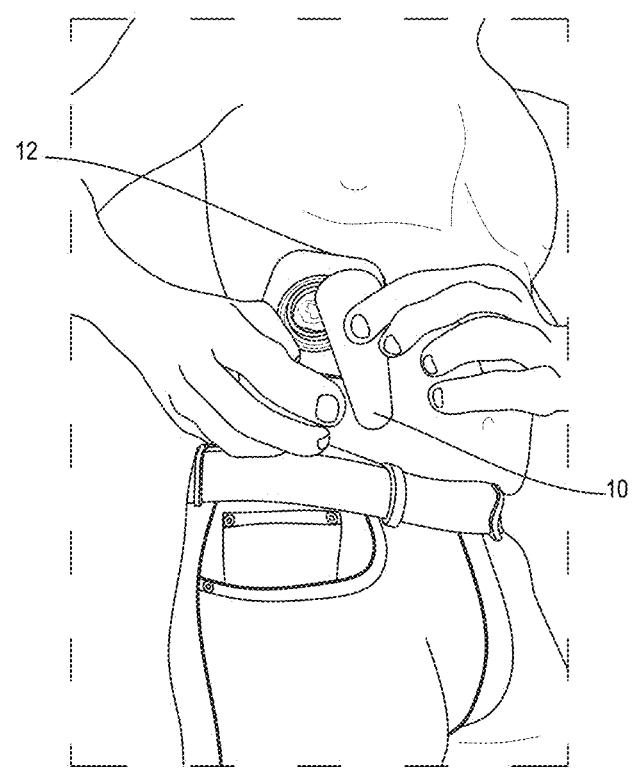
FIG. 14 shows the cupping tube detached from the patient's chest.
Figure 15:
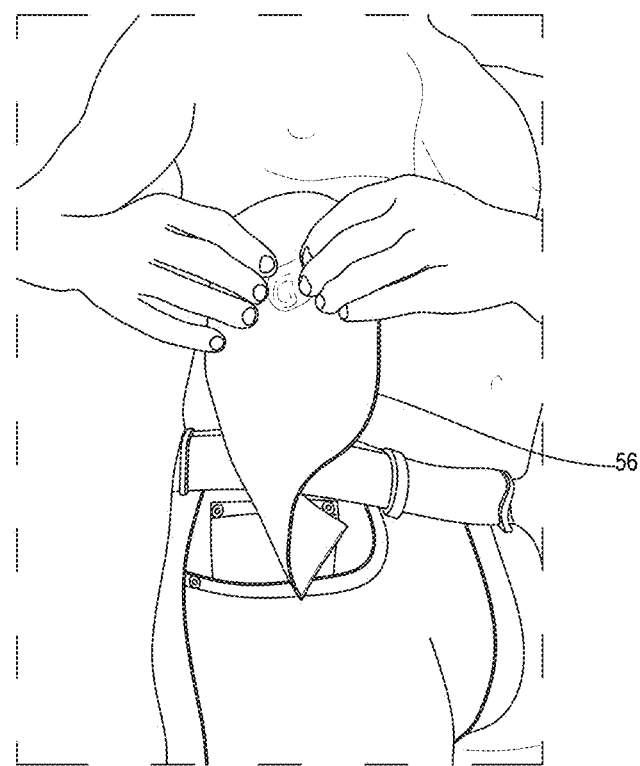
FIG. 15 is a view showing the patient attaching a collection pouch to the ring wafer.

With applicant's system, a protective strip 54 may be removed from a replacement ring wafer 12 as shown in FIG. 9 revealing an adhesive layer on the underside of the wafer. Alternatively, the adhesive may be hand applied to the wafer or to the patient's skin before the ring wafer is slid over cupping tube 10 as shown in FIG. 10. Ring wafer 12 is then positioned and pressed against the user's skin adhesively sealing the wafer in place as shown in FIG. 11-12. During all which time, urine seeping from stoma 20 is drawn into cupping tube 10 and stoma is protected from mechanical injury. Cupping tube 10 may then removed as shown in FIGS. 13-14 and a replacement pouch 46 secured to ring wafer 12 as shown in FIG. 15.

Urine is not considered a medically hazardous material. Hence cupping tube 10 filled with urine may be wrapped in a paper towel or the like and disposed of with ordinary trash. Placement of the replacement ring wafer 12 on clean, dry skin makes it less likely that the wafer will need to be changed earlier than the expected and insurance covered every 4 to 10 days of use. The procedure is also less traumatic for a patient making the change alone and for his or her caretaker if assisted. While the above focus has been on application of cupping tube 10 to a urostomy stoma similar considerations apply to use on an ileostomy or colostomy stoma.

In view of the above, it will be seen that the object of the invention is achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A cupping tube for collecting fluid from a stoma comprising a hollow cone seated on a hollow stepped conical frustrum, said cone formed of a flexible or compressible material and said stepped conical frustrum formed of a rigid, non-compressible material, said stepped conical frustrum having an upper and a lower tier, said lower tier having an outer wall with a flat upper surface upon which a base of the cone is seated, said stepped conical frustrum having an inner wall that slopes outwardly towards a base of the stepped conical frustrum at a lower angle than the outer wall makes to the lower base of the stepped conical frustrum to maximize contact area with a base of the stoma.

2. The cupping tube of claim 1 wherein a disc in inserted into an upper base of the lower tier.

3. The cupping tube of claim 2 wherein the disc has at least one perforation.

4. The cupping tube of claim 3 wherein the disc has a retaining ring around an outer edge snap fitted into a groove in an inner surface of the lower tier.

5. A cupping tube for collecting fluid from a stoma comprising a hollow cone seated on a hollow stepped conical frustrum, said cone formed of a flexible or compressible material and said stepped conical frustrum formed of a rigid, non-compressible material, said stepped conical frustrum having an upper tier an lower tier, each of said upper and lower tiers having an upper and lower circular base, said lower tier having an outer wall with a flat upper surface at the upper circular base upon which a base of the cone is seated, said lower tier having an inner wall that slopes outwardly towards the lower circular base at a lower angle than the outer wall of the lower tier makes to the lower circular base to maximize contact area with the stoma.

6. The cupping tube of claim 5 wherein the cone is formed of a reversible compressible plastic material and the stepped conical frustrum is formed of a non-compressible plastic material.

7. The cupping tube of claim 5 wherein the cone is formed of a thermoplastic elastomer.

8. The cupping tube of claim 5 wherein a disc in inserted into an upper base of the upper tier.

9. The cupping tube of claim 8 wherein the disc has at least one perforation.

10. The cupping tube of claim 9 wherein the disc has a retaining ring around an outer edge snap fitted into a groove in an inner surface of the upper tier.

\* \* \* \* \*